United States Patent [19]

Ulrich

[11] Patent Number: 5,514,664
[45] Date of Patent: May 7, 1996

[54] 1,4-DIHYDROPYRIDINES FOR APPLICAITON IN COMBATTING RESISTANCE TO DRUGS

[75] Inventor: Wolf-Rüdiger Ulrich, Konstanz, Germany

[73] Assignee: BYK Gulden Lomberg Chemische Fabrik GmbH, Konstanz, Germany

[21] Appl. No.: 949,870

[22] PCT Filed: May 22, 1991

[86] PCT No.: PCT/EP91/00957

§ 371 Date: Nov. 24, 1992

§ 102(e) Date: Nov. 24, 1992

[87] PCT Pub. No.: WO91/18599

PCT Pub. Date: Dec. 12, 1991

[30] Foreign Application Priority Data

May 26, 1990 [DE] Germany ............... 40 17 061.6
Jul. 26, 1990 [CH] Switzerland ............ 02479/90

[51] Int. Cl.$^6$ ............ A61K 31/70; A61K 31/55; A61K 31/44; A61K 35/00; A61K 31/445
[52] U.S. Cl. .............. 514/34; 514/218; 514/283; 514/318; 424/114
[58] Field of Search .............. 514/318, 283, 514/34, 218; 424/114

[56] References Cited

PUBLICATIONS

Cancer Research, vol. 50, No. 5, Mar. 1, 1990, pp. 1645–1649.
Naunyn–Schmiedeberg's Arch Pharmacol. vol. 341 (Suppl.) 1990, p. R45, abstract No. 177.
Nature, vol. 345, May 17, 1990, pp. 253–256.
Nature, vol. 345, May 17, 1990, pp. 202–203.
International Journal of Cancer, vol. 47, No. 6, Apr. 1, 1991, pp. 870–874.
Proc. Natl. Acad. Sci., vol. 84, pp. 7310–7314, Oct. 1987.
Am. J. Trop. Med Hyg. 39(1), 1988, pp. 15–20.
Cell, vol. 57, Jun. 16, 1989, pp. 921–930.
Proceedings of 81st annual meeting of the Amer. Assoc. for Cancer Research, vol. 31, Mar. 1990, p. 350 abstract only.
Carter et al., Chemotherapy of Cancer, 2nd Ed, John Wiley & Sons, N.Y., N.Y. 1981, pp. 84 & 85.

*Primary Examiner*—Jerome D. Goldberg
*Attorney, Agent, or Firm*—Jacobson, Price, Holman & Stern

[57] ABSTRACT

Optically pure diaryl compounds of formula (I), in which the substituents and symbols have the meanings indicated in the description are proposed as active ingredients in medicinal preparations for treating tumorous diseases.

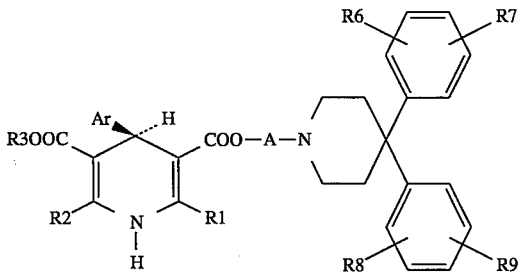

2 Claims, No Drawings

1,4-DIHYDROPYRIDINES FOR APPLICAITON IN COMBATTING RESISTANCE TO DRUGS

FIELD OF USE OF THE INVENTION

The invention relates to a new use of known dihydropyridines. The dihydropyridines can be employed in the pharmaceutical industry for the preparation of new medicaments.

KNOWN TECHNICAL BACKGROUND

The development of resistances to one or more active compounds (drug resistance, multidrug resistance =MDR) is an ever increasing problem in the therapy of certain diseases, thus, for example, in the chemotherapy of tumour diseases or in the treatment of malaria.

The use of so-called calcium antagonists, and in this context in particular 1,4-dihydropyridines, for overcoming "drug resistance" or "multidrug resistance (MDR)" has thus been under discussion for a few years [see e.g. EP-A-0 221 382; EP-A-0 353 692; M. Kamiwatari et al., Cancer Research 49, 3190 (1989); I. Nogae et al., Biochem. Pharm. 38, 519 (1989) or D. J. Krogstad et al., Science 238, 1283 (1987)]. Because of the marked influence which many of the calcium antagonists investigated have on the cardiovascular system, the search for suitable "MDR blockers" has concentrated on those 1,4-dihydropyridines which display only a mild calcium-antagonistic activity [T. Yoshinari et al., Cancer Chemother. Pharmacol. 24, 367 (1989)].

The use of certain optically pure 1,4-dihydropyridines, which have a comparatively small influence on the cardiovascular system, for the preparation of medicaments for the treatment of tumour disease is claimed in International Patent Application WO 89/07443, which corresponds to application Ser. No. 07/881,319, filed on May 7, 1992.

DESCRIPTION OF THE INVENTION

It has now been found that the 1,4-dihydropyridines described in more detail below are outstandingly capable of increasing the activity of cytostatics against tumour cells (synergism) and of overcoming the resistance of tumour cells to certain cytostatics. Surprisingly, it has also been found that overcoming of resistance is not limited to resistances to cytostatics, but that resistances to other therapeutics (e.g. for the treatment of malaria) are also overcome.

The invention therefore relates to the use of optically pure 1,4-dihydropyridines of the formula I

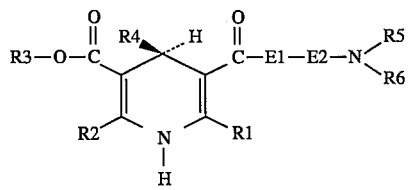

wherein

R1 denotes 1–6C-alkyl or 1–4C-alkoxy-2–4C-alkyl,

R2 denotes hydrogen, amino ($NH_2$), 1–6C-alkyl or 1–4C-alkoxy-2–4C-alkyl,

R3 denotes 1–6C-alkyl or 1–4C-alkoxy-2–4C-alkyl,

R4 denotes phenyl which is substituted by R41 and R42,

R41 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R42 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, E1 denotes oxygen (O), E2 denotes straight-chain or branched 1–5C-alkylene, the grouping $(-CH_2)_m-E-(CH_2)_n-$ or the grouping $-A1-O-A2-$, E denotes vinylene ($-CH=CH-$) or ethinylene ($-C\equiv C-$), m denotes the number 1 or 2, n denotes the number 1 or 2, A1 denotes 2–4C-alkylene, A2 denotes 2–4C-alkylene or 2C-alkylenoxy-2C-alkylene, R5 and R6, together and including the nitrogen atom to which they are both bonded, represent a radical of the formula

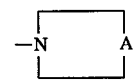

wherein

A denotes $-CH_2-CH_2-C(R7)R8-CH_2-CH_2-$, $-CH_2-CH_2-CHR9-CH_2-CH_2-$ or $-CH_2-CH_2-CHR10-$, R7 denotes hydrogen (H) or aryl and R8 denotes aryl, or R7 and R8 together denote diarylmethylene, R9 denotes diaryl-1–4C-alkyl and R10 denotes aryl-1–4C-alkyl, wherein Aryl represents a ring of the formula

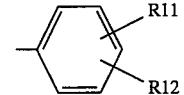

wherein R11 and R12 are identical or different and denote hydrogen (H), 1–4C-alkyl, 1–4C-alkoxy, halogen, hydroxyl, trifluoromethyl or, together, methylenedioxy, and their pharmacologically tolerated salts, for the preparation of medicaments which are to be used for improving the action of antibiotics and/or cytostatics and/or for overcoming resistances to antibiotics and/or cytostatics.

1–6C-Alkyl is straight-chain or branched and denotes, for example, a hexyl, neopentyl, isopentyl, butyl, i-butyl, sec-butyl, t-butyl, propyl, isopropyl or, in particular, ethyl or methyl radical.

1–4C-Alkyl is straight-chained or branched and denotes, for example, a butyl, i-butyl, sec-butyl, t-butyl, propyl, isopropyl, ethyl or, in particular, methyl radical.

1–4C-Alkoxy contains, in addition to the oxygen atom, one of the abovementioned 1–4C-alkyl radicals. The methoxy and the ethoxy radical are preferred.

1–4C-Alkoxy-2–4C-alkyl represents a butyl, propyl or, in particular, ethyl radical which is substituted by one of the abovementioned 1–4C-alkoxy radicals. The methoxyethyl radical is preferred.

Halogen in the context of the invention denotes bromine, fluorine and, in particular, chlorine.

1–4C-Alkoxy which is completely or partly substituted by fluorine is, for example, 1,1,2,2-tetrafluoroethoxy, trifluoromethoxy, 2,2,2-trifluoroethoxy or, in particular, difluoromethoxy.

1–4C-Alkoxycarbonyl contains, in addition to the carbonyl group, one of the abovementioned 1–4C-alkoxy radicals.

2–5C-Acyl contains, in addition to the carbonyl group, one of the abovementioned 1–4C-alkyl radicals. The acetyl radical is preferred.

Mono- or di-1–4C-alkylamino contains, in addition to the nitrogen atom, one or two of the abovementioned 1–4C-alkyl radicals. Di-1–4C-alkylamino is preferred, and here in particular dimethyl-, diethyl- or diisopropylamino.

Straight-chain or branched 1–5C-alkylene is, for example, methylene (—CH$_2$—), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 1,1-dimethylpropylene [—C(CH$_3$)$_2$—CH$_2$—CH$_2$—], 2,2-dimethylethylene [—CH$_2$—C(CH$_3$)$_2$—], isopropylidene [—C(CH$_3$)$_2$—] and 1-methylethylene [—CH(CH$_3$)—CH$_2$—].

2–4C-Alkylene represents ethylene (—CH$_2$—CH$_2$—), trimethylene —CH$_2$—CH$_2$—CH$_2$—) and tetramethylene (—CH$_2$—CH$_2$—CH$_2$—CH$_2$—), ethylene being preferred.

2C-Alkylenoxy-2C-alkylene represents ethylene which is substituted by ethylenoxy (—CH$_2$—CH$_2$—O—CH$_2$—CH$_2$—).

Aryl represents phenyl which is substituted by R11 and R12. Examples of aryl radicals which may be mentioned are the radicals: phenyl, 4-methoxyphenyl, 4-chlorophenyl, 4-methylphenyl, 4-fluorophenyl, 3-fluorophenyl, 3-chlorophenyl, 2-chlorophenyl, 3-methoxyphenyl, 2-methoxyphenyl, 2-ethoxyphenyl, 2-methylphenyl, 3-chloro-4-methylphenyl, 3,4-dichlorophenyl, 3,6-dichlorophenyl, 2,4-dimethylphenyl, 2,6-dimethylphenyl, 3,4-dimethylphenyl, 3,4-methylenedioxyphenyl, 2-trifluoromethylphenyl and 3-trifluoromethylphenyl.

Diaryl-1–4C-alkyl is 1–4C-alkyl which is substituted by two aryl radicals. Diaryl-1–4C-alkyl is, in particular, diphenylmethyl (benzhydryl), or substituted benzhydryl, such as e.g. 4,4'-difluorobenzhydryl, 4,4'-dimethylbenzhydryl, 4,4'-dimethoxybenzhydryl or 4,4'-dichlorobenzhydryl.

Aryl-1–4C-alkyl is 1–4C-alkyl which is substituted by aryl. Benzyl and 4-chlorobenzyl may be mentioned in particular.

Possible salts are all the salts with acids. The pharmacologically tolerated salts of the inorganic and organic acids which are customarily used in the pharmaceutical industry may be mentioned in particular. Suitable such salts are, for example, water-soluble and water-insoluble acid addition salts, such as the hydrochloride, hydrobromide, hydriodide, phosphate, nitrate, sulphate, acetate, citrate, gluconate, benzoate, hibenzate, fendizoate, butyrate, sulphosalicylate, maleate, laurate, malate, fumarate, succinate, oxalate, tartrate, amsonate, metembonate, stearate, tosylate, 3-hydroxy-2-naphthoate or mesylate.

As the antibiotics, the action of which is improved or towards which resistance is overcome there may be mentioned primarily those antibiotics in which a (growing) development of resistance is to be observed. In this connection there may be mentioned, for example, antibiotics against bacteria, mycoses, viruses and parasites, in particular against sporozoa, and here above all malaria agents, such as, for example, amodiaquine, mefloquine, pamaquine, primaquine, tebuquine, hydroxychloroquine and, in particular, chloroquine.

The cytostatics, the action of which is improved synergistically or towards which resistance is overcome are all the customary cytostatics, such as, for example, alkylating agents of the nitrogen lost derivative type (e.g. chlorambucil, cyclophosphamide or ifosfamide) or of the platinum complex type (e.g. cisplatin, carboplatin, iproplatin, oxaliplatin, oxoplatin, spiroplatin or tetraplatin), or intercalating substances of the anthracycline type (e.g. aclarubicin, daunorubicin, doxorubicin, esorubicin, epirubicin, idarubicin, pirarubicin or zorubicin), or mitopodozides (e.g. etoposide), or vinca alkaloids (e.g. vinblastine, vincristine, vinedesine, vinepidine, vinleurosine, vinorelbine, vinrosidine, vintriptole or vinzolidine).

One embodiment (embodiment a) of the invention is the use of optically pure 1,4-dihydropyridines of the formula I, wherein R1 denotes 1–6C-alkyl or 1–4C-alkoxy-2–4C-alkyl, R2 denotes hydrogen, amino (NH$_2$), 1–6C-alkyl or 1–4C-alkoxy-2–4C-alkyl, R3 denotes 1–6C-alkyl or 1–4C-alkoxy-2–4C-alkyl, R4 denotes phenyl which is substituted by R41 and R42, R41 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R42 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, E1 denotes oxygen (O), E2 denotes straight-chain or branched 1–5C-alkylene or the grouping —A1—O—A2—, A1 denotes 2–4C-alkylene A2 denotes 2–4C-alkylene or 2C-alkylenoxy-2C-alkylene R5 and R6, together and including the nitrogen atom to which they are both bonded, represent a radical of the formula

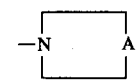

wherein
A denotes —CH$_2$—CH$_2$—C(R7)R8—CH$_2$—CH$_2$—,
R7 denotes aryl and
R8 denotes aryl, wherein
  Aryl represents a ring of the formula

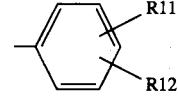

wherein R11 and R12 are identical or different and denote hydrogen (H), 1–4C-alkyl, 1–4C-alkoxy, halogen, hydroxyl, trifluoromethyl or, together, methylenedioxy, and their pharmacologically tolerated salts for the preparation of medicaments which are to be used for improving the action of antibiotics and/or cytostatics and/or for overcoming resistances towards antibiotics and/or cytostatics.

A further embodiment (embodiment b) of the invention is the use of optically pure 1,4-dihydropyridines of the formula I, wherein R1 denotes 1–6C-alkyl or 1–4C-alkoxy-2–4C-alkyl, R2 denotes hydrogen, amino (NH$_2$), 1–6C-alkyl or 1–4C-alkoxy-2–4C-alkyl, R3 denotes 1–6C-alkyl or 1–4C-alkoxy-2–4C-alkyl, R4 denotes phenyl which is substituted by R41 and R42, R41 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R42 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, E1 denotes oxygen (O), E2 denotes the grouping —(CH$_2$)$_m$—E—(CH$_2$)$_n$—, E denotes vinylene (—CH=CH—) or ethynylene (—C≡C—), m denotes the number 1 or 2, n denotes the number 1 or 2, R5 and R6, together and including the nitrogen atom to which they are both bonded, represent a radical of the formula

wherein

A denotes —CH$_2$—CH$_2$—C(R7)R8—CH$_2$—CH$_2$—, —CH$_2$—CH$_2$—CHR9—CH$_2$—CH$_2$— or —CH$_2$—CH$_2$—CH$_2$—CHR10—, R7 denotes hydrogen (H) or aryl and R8 denotes aryl, or R7 and R8 together denote diarylmethylene, R9 denotes diaryl-1–4C-alkyl and R10 denotes aryl-1–4C-alkyl, wherein Aryl represents a ring of the formula

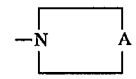

wherein R11 and R12 are identical or different and denote hydrogen (H), 1–4C-alkyl, 1–4C-alkoxy, halogen, hydroxyl, trifluoromethyl or, together, methylenedioxy, and their pharmacologically tolerated salts for the preparation of medicaments which are to be used for improving the action of antibiotics and/or cytostatics and/or for overcoming resistances towards antibiotics and/or cytostatics.

A further embodiment (embodiment c) of the invention is the use of optically pure 1,4-dihydropyridines of the formula I, wherein R1 denotes 1–6C-alkyl or 1–4C-alkoxy-2–4C-alkyl, R2 denotes hydrogen, amino (NH$_2$), 1–6C-alkyl or 1–4C-alkoxy-2–4C-alkyl, R3 denotes 1–6C-alkyl or 1–4C-alkoxy-2–4C-alkyl, R4 denotes phenyl which is substituted by R41 and R42, R41 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R42 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, E1 denotes oxygen (O), E2 denotes straight-chain or branched 1–5C-alkylene, the grouping —(CH$_2$)$_m$—E—(CH$_2$)$_n$— or the grouping —A1—O—A2—, E denotes vinylene (—CH=CH—) or ethynylene (—C≡C—), m denotes the number 1 or 2, n denotes the number 1 or 2, A1 denotes 2–4C-alkylene, A2 denotes 2–4C-alkylene or 2C-alkylenoxy-2C-alkylene, R5 and R6, together and including the nitrogen atom to which they are both bonded, represent a radical of the formula

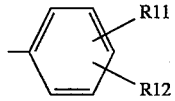

wherein

A denotes —CH$_2$—CH$_2$—C(R7)R8—CH$_2$—CH$_2$—, —CH$_2$—CH$_2$—CHR9—CH$_2$—CH$_2$— or —CH$_2$—CH$_2$—CH$_2$—CHR10—, R7 denotes hydrogen (H) and R8 denotes aryl, or R7 and R8 together denote diarylmethylene, R9 denotes diaryl-1–4C-alkyl and R10 denotes aryl-1–4C-alkyl, wherein Aryl represents a ring of the formula

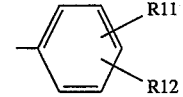

wherein R11 and R12 are identical or different and denote hydrogen (H), 1–4C-alkyl, 1–4C-alkoxy, halogen, hydroxyl, trifluoromethyl or, together, methylenedioxy, and their pharmacologically tolerated salts for the preparation of medicaments which are to be used for improving the action of antibiotics and/or cytostatics and/or for overcoming resistances towards antibiotics and/or cytostatics.

Subject matter of the invention which is to be singled out is the use according to the invention of compounds of the formula I, wherein R1 denotes 1–4C-alkyl, R2 denotes 1–4C-alkyl, R3 denotes 1–4C-alkyl, R4 denotes phenyl which is substituted by R41 and R42, R41 denotes hydrogen, chlorine or nitro, R42 denotes hydrogen or chlorine, E1 denotes oxygen, E2 denotes ethylene or propylene, R5 and R6, together and including the nitrogen atom to which they are both bonded, represent a radical of the formula

wherein

A denotes —CH₂—CH₂—C(R7)R8—CH₂—CH₂—, —CH₂—CH₂—CHR9—CH₂—CH₂— or —CH₂—CH₂—CH₂—CHR10—, R7 denotes hydrogen or phenyl and R8 denotes phenyl, or R7 and R8 together denote diphenylmethylene, R9 denotes diphenylmethyl (benzhydryl) and R10 denotes benzyl or 4-chlorobenzyl, and their pharmacologically tolerated salts.

Subject matter of the invention which is to be especially singled out is the use according to the invention of compounds of embodiments a, b and c, wherein the substituents and symbols have the meanings given for the subject matter of the invention which is to be singled out.

Preferred subject matter of the invention is the use according to the invention of compounds of the formula I, wherein R1 denotes 1–4C-alkyl, R2 denotes 1–4C-alkyl, R3 denotes 1–4C-alkyl, R4 denotes 3-nitrophenyl, E1 denotes oxygen, E2 denotes ethylene or propylene, R5 and R6, together and including the nitrogen atom to which they are both bonded, represent a radical of the formula

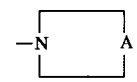

wherein

A denotes —CH₂—CH₂—C(R7)R8—CH₂—CH₂—,

R7 denotes phenyl and

R8 denotes phenyl, and their pharmacologically tolerated salts.

Compounds which are particularly suitable for the use according to the invention can be seen from the following Table I, in which the corresponding compounds of the formula I are shown with the particular substituent definitions:

TABLE I $$\underset{R2}{\underset{|}{\overset{R3-O-\overset{O}{\overset{\|}{C}}}{}}}\underset{\underset{H}{\overset{|}{N}}}{\overset{R4\diagdown\;,H}{\bigcirc}}\overset{\overset{O}{\overset{\|}{C}}-E1-E2-N\diagup^{R5}_{\diagdown R6}}{\underset{R1}{}} \quad (I)$$

| R1 | R2 | R3 | R4 | —E1—E2— | —N(R5)(R6) |
|---|---|---|---|---|---|
| CH₃ | CH₃ | CH₃ | 3-NO₂-phenyl | —O—CH₂—CH₂—CH₂— | 4,4-diphenylpiperidin-1-yl |
| CH₃ | CH₃ | CH₃ | 2,3-dichlorophenyl | —O—CH₂—CH₂—CH₂— | 4,4-diphenylpiperidin-1-yl |

TABLE I-continued

Structure (I):

R3—O—C(=O)—[C(R4)(H) in dihydropyridine ring]—C(=O)—E1—E2—N(R5)(R6)

with R2 and R1 at the 6- and 2-positions of the 1,4-dihydropyridine (NH).

| R1 | R2 | R3 | R4 | —E1—E2— | —N(R5)(R6) |
|---|---|---|---|---|---|
| CH₃ | CH₃ | CH₃ | 2-Cl-phenyl | —O—CH₂—CH₂—CH₂— | —N(piperidine-4,4-diyl)(diphenyl) (4,4-diphenylpiperidin-1-yl) |
| CH₃ | CH₃ | CH₃ | 3-NO₂-phenyl | —O—CH₂—CH₂— | 4,4-diphenylpiperidin-1-yl |
| CH₃ | CH₃ | CH₃ | 3-NO₂-phenyl | —O—CH₂—CH₂—CH₂— | 4-(diphenylmethylene)piperidin-1-yl |
| CH₃ | CH₃ | CH₃ | 3-NO₂-phenyl | —O—CH₂—CH₂—CH₂— | 4-phenylpiperidin-1-yl |
| CH₃ | CH₃ | CH₃ | 3-NO₂-phenyl | —O—CH₂—CH₂—CH₂— | 4-(diphenylmethyl)piperidin-1-yl |

*Note: R1 values shown as CH₃ (written as $CH_3$); NO₂ as $NO_2$.*

TABLE I-continued

Structure (I):

$$R_3-O-\underset{\underset{R_2}{\|}}{\overset{O}{C}}-\underset{\underset{\underset{H}{N}}{}}{\overset{R_4\;\;H}{C}}-\underset{\underset{R_1}{\|}}{\overset{O}{C}}-E_1-E_2-N\underset{R_6}{\overset{R_5}{\diagup}}$$

| R1 | R2 | R3 | R4 | —E1—E2— | —N(R5)(R6) |
|---|---|---|---|---|---|
| CH₃ | CH₃ | CH₃ | 3-NO₂-phenyl | —O—CH₂—CH₂—CH₂— | 2-benzylpyrrolidinyl |
| CH₃ | CH₃ | CH₃ | 3-NO₂-phenyl | —O—CH₂—CH₂—CH₂— | 2-(4-chlorobenzyl)pyrrolidinyl |
| CH₃ | CH₃ | CH₃ | 3-NO₂-phenyl | —O—CH₂—CH=CH—CH₂— | 4,4-diphenylpiperidinyl |
| CH₃ | CH₃ | CH₃ | 3-NO₂-phenyl | —O—CH₂—C≡C—CH₂— | 4,4-diphenylpiperidinyl |
| CH₃ | CH₃ | CH₃ | 3-NO₂-phenyl | —O—(CH₂)₂O(CH₂)₂— | 4,4-diphenylpiperidinyl |

The compounds of the formula I are known, for example from EP-A-242 829, EP-A-296 316, DE-OS 36 27 742 and WO88/07531.

COMMERCIAL USEFULNESS

The compounds of the formula I and their pharmacologically tolerated salts have useful properties which render them commercially usable in the context according to the invention. They improve the action of antibiotics and cytostatics in a synergistic manner, and moreover they are capable of overcoming resistances towards antibiotics and cytostatics which already exist or occur in the course of therapy.

The invention thus relates to the use of compounds of the formula I in combination with antibiotics or cytostatics in antibiotic and/or cytostatic therapy.

The invention furthermore relates to the use of compounds of the formula I for the preparation of medicaments which are to be employed in combination with antibiotics or cytostatics in antibiotic and/or cytostatic therapy.

In overcoming resistance towards antibiotics, it is of particular importance to overcome resistance towards chloroquine, since the increasing development of resistance of Plasmodium falciparum (the pathogen of malaria tropica) towards this proven malaria agent in some parts of the world presents increasing difficulties in combating malaria.

In improving the action of or overcoming the development of resistance towards cytostatics, it is of particular importance that the dose of the cytostatics administered can be reduced, which leads to a significant reduction in toxic side effects, and that the number of cytostatics which can be employed is increased, so that the cytostatic of optimum suitability for the particular tumour and the particular patient can be selected in a targeted manner.

It should be pointed out in this connection that because of the small influence of the compounds I on the cardiovascular system, e.g. on blood pressure and heart rate, these compounds can be administered in therapeutically active doses without the risk of undesirable side effects on the cardiovascular system.

The excellent activity of compounds of the formula I and their pharmacologically tolerated salts enables them to be used in human medicine as active compounds in antibiotic and cytostatic therapy, it being possible for the compounds of the formula I to be administered together with the antibiotics or cytostatics in a specified dose in the form of combination preparations, or it being possible for the compounds of the formula I to be employed separately, in any desired dosage and a suitable presentation form, as concomitant and assisting active compounds in antibiotic or cytostatic therapy.

The ratio of compound I to antibiotic or cytostatic depends on the disease to be treated, the state of the disease in the patient and the antibiotic or cytostatic used. It has in general proved advantageous here to administer the compounds of the formula I in a daily dose of about 0.5 to 30 mg/kg of body weight for oral administration and in a daily dose of about 0.1 to 10 mg/kg of body weight for intravenous administration, if desired in the form of several individual doses or as a continuous infusion, in order to achieve the desired result. The antibiotics or cytostatics are administered in the doses customary for them, but preferably in lower doses.

The particular optimum dosage and mode of administration required for the active compounds can be specified by any expert on the basis of his expert knowledge.

BIOLOGICAL TESTING

The ability of compounds of the formula I to overcome the resistance of tumour cells towards cytostatics was demonstrated on various tumour cell lines.

For this, a selected compound of the formula I, the compound (−)-1,4-dihydro-2,6-dimethyl-4-(3-nitrophenyl)-pyridine-3,5-dicarboxylic acid 3-methyl 5-[3(4,4-diphenyl-1-piperidinyl)-propyl] ester hydrochloride (=compound 1), was investigated in more detail as follows:

The tumour cell lines MOLT/VCR-5×9 (starting density: $1.14\times10^6$ cells/ml), MOLT/DAU-8 (starting density: $1.01\times10^6$ cells/ml) and CCRF CEMVCR1000+(starting density: $2.00\times10^6$ cells/ml), which are resistant towards the cytostatics vincristine and daunomycin, were incubated for 72.5 to 73.25 hours in accordance with the following test pattern:

1. Control, without active compound
2. Control with the cytostatic relating to the particular cell line (for the concentrations, see below)
3. Control with 1% DMSO
4. Compound 1 in concentrations of $10^{-6}$ and $10^{-7}$M
5. Compound 1 in concentrations of $10^{-6}$ and $10^{-7}$M, together with the cytostatic relating to the particular cell line (for the concentrations, see below).

The cytostatic concentrations used for the individual cell lines were:

Vincristine: $5\times10^{-9}$M (for MOLT/VCR-5×9)

Daunomycin: $10^{-8}$M (for MOLT/DAU-8)

Vincristine: $1.08\times10^{-6}$M (for CCRF CEM VCR1000+)

The percentage reduction in cell counts (given in % of the DMSO control) on addition of the cytostatic by itself, compound 1 in concentrations of $10^{-7}$M or $10^{-6}$M by itself, and cytostatic+compound 1 in concentrations of $10^{-7}$M or $10^{-6}$M is as shown in Table 2:

TABLE 2

Intensification of the cytotoxicity of cytostatics by compound 1; percentage growth inhibition of tumour cell lines in comparison with the DMSO control

| Cell line:<br>Cytostatic:<br>[concentration]<br>Active compound [concentration] | MOLT/VCR-<br>5 × 9<br>Vincristine<br>[5 × $10^{-9}$M] | MOLT/DAU-8<br>Daunomycin<br>[$10^{-8}$M]<br>Growth inhibition in % | CCRF CEM VCR1000 +<br>Vincristine<br>[1.08 × $10^{-6}$M] |
|---|---|---|---|
| Cytostatic by itself | 0 | 0 | 0 |
| Compound 1 [$10^{-7}$M] by itself | 66 | 43 | 10 |
| Compound 1 [$10^{-7}$M] + cytostatic | 99 | 56 | 65 |
| Compound 1 p$10^{-5}$M] by itself | 79 | 53 | 67 |
| Compound 1 [$10^{-5}$M] + | 99 | 96 | 90 |

TABLE 2-continued

Intensification of the cytotoxicity of cytostatics by compound 1; percentage
growth inhibition of tumour cell lines in comparison with the DMSO control

| Cell line:<br>Cytostatic:<br>[concentration]<br>Active compound [concentration] | MOLT/VCR-<br>5 × 9<br>Vincristine<br>$[5 \times 10^{-9}M]$ | MOLT/DAU-8<br>Daunomycin<br>$[10^{-8}M]$<br>Growth inhibition in % | CCRF CEM VCR1000 +<br>Vincristine<br>$[1.08 \times 10^{-6}M]$ |
|---|---|---|---|
| cytostatic | | | |

The following can be seen from the values shown in Table 2:

When the cytostatics are added by themselves, no growth inhibition at all is to be observed, and the tumour cell lines are resistant towards the cytostatics.

All resistant cells are inhibited in their growth by addition of compound 1 by itself. This inhibition of growth depends on the concentration.

By addition of compound 1 together with the cytostatic, the resistance towards cytostatics is overcome and the cytotoxicity of the cytostatics is intensified.

I claim:

1. A medicament composition which comprises, in addition to an effective amount of the active ingredient selected from the group consisting of vincristine, daunomycin, doxorubicin and etoposide, a synergistically-effective amount of optically-pure (R)-(+)-1,4-dihydro- 2,6-dimethyl-4-(3-nitrophenyl)-pyridine-3,5-dicarboxylic acid 3-methyl 5-[3-(4,4-diphenyl-1-piperidinyl)-propyl]ester, or a pharmacologically-tolerated salt thereof, to improve the action of or to overcome resistance to the active ingredient.

2. A method of synergistically improving action of or overcoming resistance toward a medicament composition used in therapy and comprising, as active component, an effective amount of a member selected from the group consisting of vincristine, daunomycin, doxorubicin and etoposide, which comprises administering to a patient in need of such therapy a synergistically-effective amount of optically-pure (R)-(+)-1,4-dihydro- 2,6-dimethyl-4-(3-nitrophenyl)-pyridine-3,5-dicarboxylic acid 3-methyl 5-[3-(4,4-diphenyl-1-piperidinyl)-propyl]ester or a pharmacologically-tolerated salt thereof, in addition to the medicament composition.

* * * * *